United States Patent
Hammerlund

[19]

[11] Patent Number: 6,164,965
[45] Date of Patent: Dec. 26, 2000

[54] PROPHYLAXIS PASTE HOLDER RING AND METHOD OF MANUFACTURE

[75] Inventor: Gary M. Hammerlund, Grand Rapids, Mich.

[73] Assignee: NuView Technologies, Inc., Grand Rapids, Mich.

[21] Appl. No.: 09/457,962

[22] Filed: Dec. 9, 1999

[51] Int. Cl.[7] .............................. A61C 1/14; A41D 19/00
[52] U.S. Cl. ............................ 433/49; 433/163; 224/217
[58] Field of Search ...................... 433/49, 163; 224/217

[56] References Cited

U.S. PATENT DOCUMENTS

| | | | |
|---|---|---|---|
| 1,462,714 | 7/1923 | Marchand | 224/217 |
| 1,555,004 | 9/1925 | Gregory | 224/217 |
| 2,072,851 | 3/1937 | Bailey | 224/217 |
| 2,222,741 | 11/1940 | Bush | 433/163 |
| 3,666,372 | 5/1972 | Lipkowski | 224/217 |
| 5,009,056 | 4/1991 | Porteous | 53/412 |
| 5,016,795 | 5/1991 | Porteous | 224/217 |
| 5,048,731 | 9/1991 | Moreschini | 222/541 |
| 5,112,227 | 5/1992 | Bull | 433/163 |
| 5,169,315 | 12/1992 | Bull | 433/163 |
| 5,732,862 | 3/1998 | Bull | 224/217 |
| 5,947,278 | 9/1999 | Sawhney et al. | 206/216 |

*Primary Examiner*—John J. Wilson
*Attorney, Agent, or Firm*—Price, Heneveld, Cooper, DeWitt & Litton

[57] ABSTRACT

Providing a finger ring retainer for a container of prophylaxis dental paste from elongated formable material segments, each segment having two end portions and a central portion, the two end portions having arcuate configurations greater than 180° in extent so that one end portion can be fitted onto a human finger and the second end portion can be fitted onto a container of dental paste, the central portion being bent at an approximately 45° apex angle sufficient to create a pair of doubled over layers of said central portion extending generally normal to each other in substantially parallel planes.

12 Claims, 3 Drawing Sheets

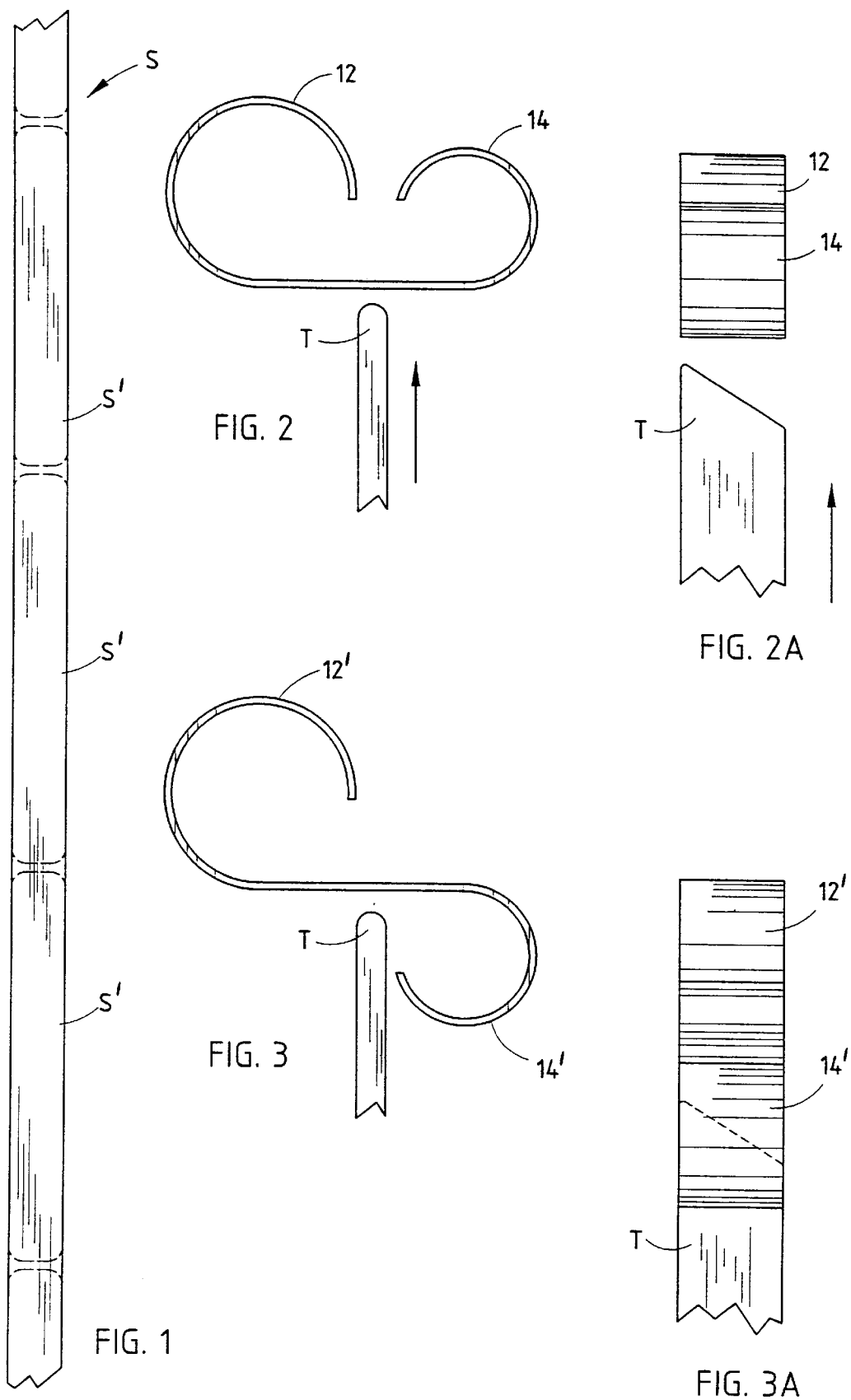

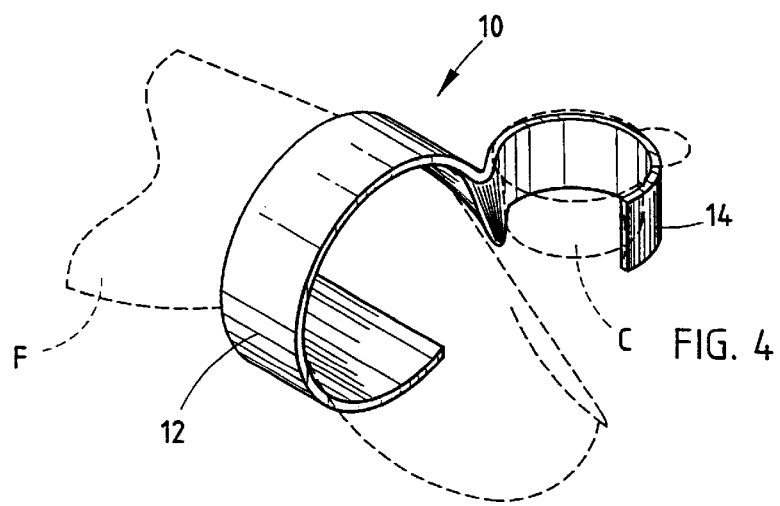
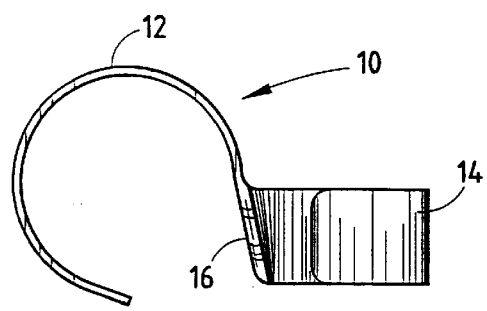
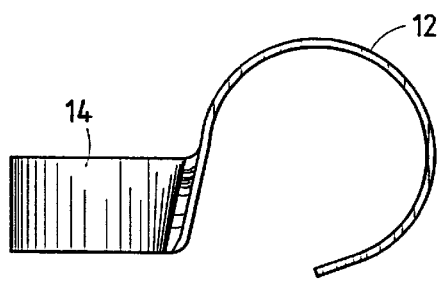
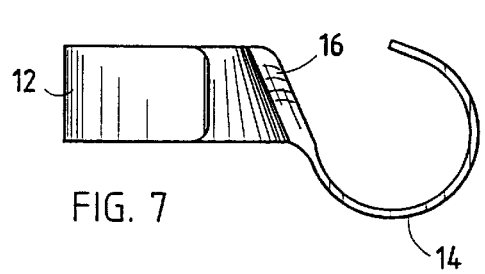
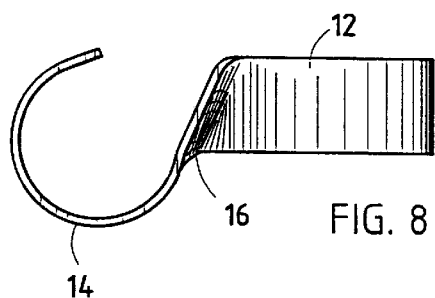
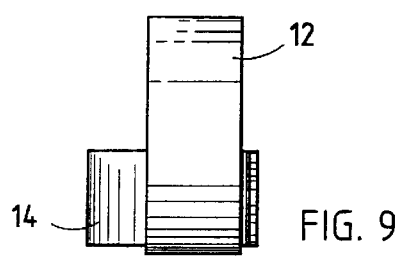
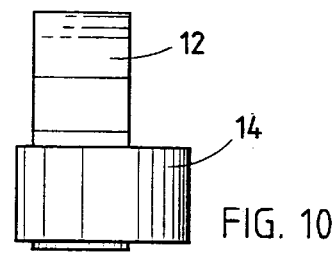

PROPHYLAXIS PASTE HOLDER RING AND METHOD OF MANUFACTURE

BACKGROUND OF THE INVENTION

Prior to the 1960's, slightly abrasive, dental prophylaxis paste used by dental practitioners, i.e., dentists or dental hygienists, to clean teeth of patients was prepared in situ at the time needed, by mixing a dry abrasive material with a wetting agent. This was typically done by a dental assistant. Because this required preparation time, a practicing dentist in the 1960's developed a product which was previously mixed into a paste and placed in small, cylindrical, cup-shaped containers having peripheral flanges, each cup being approximately one-half inch in diameter and having a sterile removable cover sheet thereover. These were prepared and sold to dentists in substantial numbers. A large number of these containers were actually formed simultaneously in each sheet of polymeric sheet stock, the containers then being filled en masse and covered with a removable sterile adhesive sheet. The multiple of containers in the sheet were separated along die cut patterns so that each prophylaxis paste cup-type container could be utilized individually.

To hold the small prophylaxis paste containers when cleaning teeth using a conventional powered buffing tool, a finger ring retainer of the type shown in FIG. 11 was developed and provided. These finger ring retainers were made by forming a sheet of metal into L-shaped segments with a punch press (FIGS. 12 and 13), i.e., each segment having a pair of legs, deburring the segments to rid them of the die cut sharp edges, cleaning the punch press oil from the segments, polishing the segments, and then bending the legs of the individual segments into arcuate, almost circular, configurated ends, so that one end would hold the prophylaxis cup and the other end could be placed around a finger of the dental practitioner.

These ring forming procedures resulted in considerable processing costs for the multiple steps required, and resulted in substantial scrap metal around the L-shaped stampings. Molded polymeric alternatives to this earlier metal ring were also provided to the market in recent years.

SUMMARY OF THE INVENTION

The present invention provides a novel method of forming a dental prophylaxis paste retention ring of deformable material, preferably metal stock. A continuous narrow strip of burr-free stock of a width equal to that of the final ring is cut into segment lengths, each segment having a pair of end portions which are subsequently curled into arcuate configurations. Each segment also has a central portion which is deformed by a slide former at an angle, preferably a 45° slide former, to bend the central portion into a doubled over pair of strip layers extending generally normal to each other in substantially parallel planes, to cause the curled end portions of the segment to be in planes generally normal to each other. The resulting novel finger ring has desirable characteristics capable of being formed at less cost and with less scrap.

These and other features, advantages and objects of the present invention will be further understood and appreciated by those skilled in the art by reference to the following specification, claims and appended drawings.

BRIEF DESCRIPTION OF THE DRAWINGS

FIG. 1 is an elevational view of a narrow continues strip of burr-free stock in accordance with this invention;

FIG. 2 is a top plan view of one embodiment of a segment separated from the strip stock and being formed into the novel finger ring;

FIG. 2A is a side elevational view of the slide forming tool in FIG. 2;

FIG. 3 is a top plan view of a second embodiment of a separated segment being formed into a ring;

FIG. 3A is a side elevational view of the slide forming tool in FIG. 3;

FIG. 4 is a perspective view of the novel finger ring formed according to this invention;

FIG. 5 is a side elevational view of the finger ring in FIG. 4;

FIG. 6 is a side elevational view of the opposite side of the finger ring in FIG. 5;

FIG. 7 is a bottom view of the finger ring in FIG. 5;

FIG. 8 is a bottom view of the finger ring as shown in FIG. 6;

FIG. 9 is an end elevational view of the finger ring in FIG. 5;

FIG. 10 is an end elevational view of the finger ring as depicted in FIG. 6;

DETAILED DESCRIPTION OF PREFERRED EMBODIMENT

Figure 11:
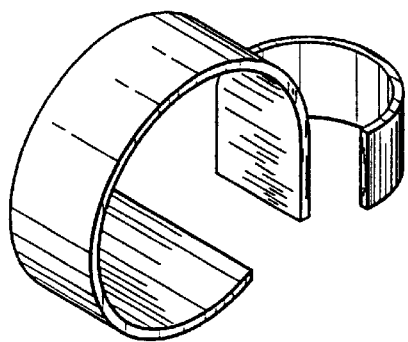
FIG. 11 is a perspective view of the prior art finger ring.
Figure 13:
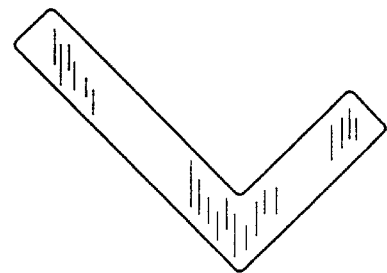
FIG. 13 is a top elevational view of one of the prior art L-shaped segments in FIG. 12.
Figure 12:
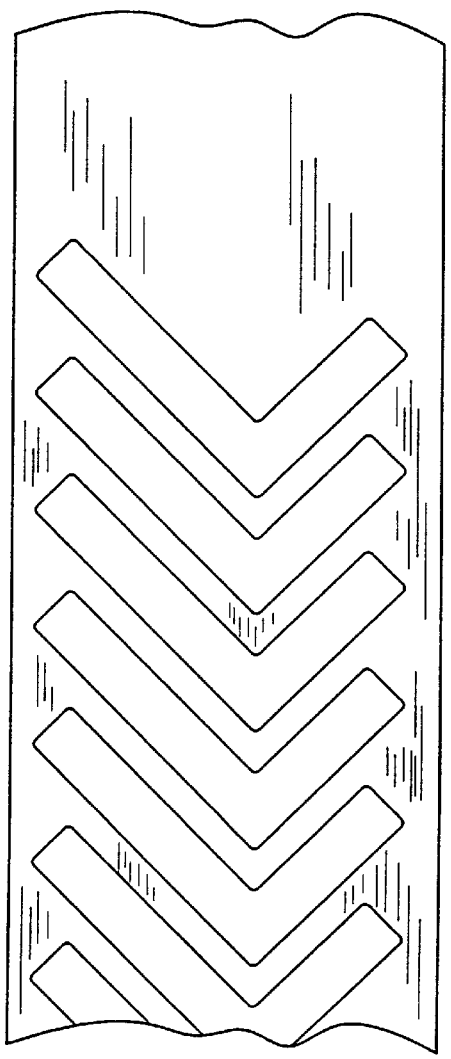
FIG. 12 is a plan view of a continuous strip of stock from which the prior art finger ring L-shaped segments were formed as by a punch press.

Referring now to the drawings, FIG. 1 depicts a continuous strip S of narrow elongated formable material, preferably stainless steel, having a width equal to that of the final ring product to be formed, and having a pair of parallel, burr-free, i.e., coined, burrless, rolled edges. The strip is cut into a plurality of segments S' as by die cutting each segment with a slightly convex curvature at its opposite ends. As a result, only a tiny bit of scrap is formed between the adjacent segment ends. Each segment is then formed into the final ring product 10 (FIGS. 4–10).

More specifically, viewing each segment as having two end portions and a central portion, the two ends portions are curled into two near-circular configurations, i.e., generally arcuate, configurations 12 and 14, greater than 180° in extent. These arcuate configurations can be formed by conventional tooling in a manner to cause both of the arcuate configurations to be on the same side of the central portion, i.e., oriented toward each other as depicted in FIG. 2, or alternatively can be formed on opposite sides of the central portion to be opposite each other as in FIG. 3. These two configurations may be of different diameters, typically with a larger one 12 to fit onto a human adult finger, and a smaller one 14 to receive a typical prophylaxis paste cup of the type which is well known in the market. Whether the two configurations are on the same side as in FIG. 2, or on opposite sides of the central portion as at 12' and 14' in FIG. 3, they are basically in the same plane prior to reforming the central portions.

The central portion of the strip segment is reformed to cause the two curvilinear end portions to be in planes generally normal to each other. This is achieved by pressing against the central portion a slide forming tool T having its leading edge in a 45° angle to the direction of slide tool movement, and a 45° angle relative to the plane of the segment central portion. This reforming step causes torsional bending forces to be applied to the central portion of the strip, creating a central bend zone 16 of double layer material as depicted in FIGS. 4–10, with the curvilinear end portions thus being moved into planes which are normal to each other. Thus, the ring can be employed as depicted in FIG. 4, i.e., with the larger curvilinear end portion 12 fitting onto a human finger F and the smaller curvilinear end portion 14 receiving and fitting around a prophylaxis paste cup C. Whether the configuration depicted in FIG. 2 or that in FIG. 3 is employed, a similar forming tool T will cause this torsional force and bending of the central portion of the segment.

Instead of the segment cut from strip S being first formed with the two curvilinear end portions and then reformed with the slide tool, alternatively the forming tool T may first form the doubled over bend in the center portion and the curvilinear end portions formed thereafter. Or, one end portion may be curvilinearly formed, the center portion then folded into the doubled over configuration, and then the second end portion formed into a curvilinear shape.

The resulting dental finger ring has several advantages over the prior art. The strip stock is formed with smooth rolled edges having no burrs so that deburring is not necessary. Cleaning and polishing is not necessary. No secondary forming is necessary. Simple slide forming can be employed. A logo can be easily and inexpensively stamped into the segments. The tooling costs are lower. And, there is little or no scrap resulting.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

The invention claimed is:

1. A method of forming a finger ring retainer for a container of prophylaxis dental paste comprising the steps of:

supplying a continuous strip of elongated formable material;

separating said strip into elongated segments, each segment having two end portions and a central portion;

curling said two end portions into generally arcuate configurations each greater than 180° in extent so that one end portion can be fitted onto a human finger and the second end portion can be fitted onto a container of dental paste; and bending said central portion at an approximately 45° apex angle sufficient to cause a pair of doubled over layers of said central portion to extend generally normal to each other.

2. The method in claim 1 wherein said bending step is achieved by forcing a 45° slide former against said central portion to bend said central portion into doubled over layers generally normal to each other.

3. The method in claim 2 wherein said strip segments are of thin formable metal.

4. The method in claim 3 wherein said continuous strip has burr free rolled edges.

5. The method in claim 1 wherein said ring shaped end portions extend toward each other prior to said bending step.

6. The method in claim 1 wherein said ring shaped end portions extend opposite each other prior to said bending step.

7. The method in claim 1 wherein said curling step is performed prior to said bending step.

8. The method in claim 1 wherein said bending step is performed prior to said curling step.

9. The method in claim 1 wherein said curling step of one of said end portions is performed prior to said bending step, and said curling step of said second end portion is performed subsequent to said bending step.

10. A finger ring retainer for a container of prophylaxis dental paste, said finger ring retainer being formed of an elongated strip and comprising:

a unitary band having two interconnected ring-shaped end portions, one of said ring-shaped end portions being in a plane generally normal to the plane of the second of said ring-shaped end portions;

a juncture central portion between and integrally joining said end portions, said juncture central portion comprising doubled over layers of said elongated strip, said layers being joined at about a 45° bend to cause said end portions to be generally normal to each other.

11. The finger ring retainer in claim 10 of thin formable metal.

12. The finger ring retainer in claim 11 having burr-free edges.

* * * * *